US008415454B2

(12) United States Patent
Joshi et al.

(10) Patent No.: US 8,415,454 B2
(45) Date of Patent: Apr. 9, 2013

(54) PROCESS FOR THE MANUFACTURE OF PEPTIDES

(75) Inventors: Satish Joshi, Palos Verdes Estates, CA (US); Shima Joshi, Palos Verdes Estates, CA (US); Bernhard Freimann, Gardena, CA (US); Manuel Ramos, Cypress, CA (US); Roland Callens, Grimbergen (BE)

(73) Assignee: Solvay (Société Anonyme), Brussels (BE)

( * ) Notice: Subject to any disclaimer, the term of this patent is extended or adjusted under 35 U.S.C. 154(b) by 0 days.

(21) Appl. No.: 12/374,344

(22) PCT Filed: Jul. 17, 2007

(86) PCT No.: PCT/EP2007/057362
§ 371 (c)(1),
(2), (4) Date: Jan. 19, 2009

(87) PCT Pub. No.: WO2008/009672
PCT Pub. Date: Jan. 24, 2008

(65) Prior Publication Data
US 2009/0326195 A1 Dec. 31, 2009

Related U.S. Application Data

(60) Provisional application No. 60/832,649, filed on Jul. 21, 2006.

(51) Int. Cl.
*C07K 1/00* (2006.01)
*C07K 1/04* (2006.01)

(52) U.S. Cl. ........ 530/333; 530/334; 530/317; 514/21.1

(58) Field of Classification Search .................. None
See application file for complete search history.

(56) References Cited

U.S. PATENT DOCUMENTS 7,250,397 B2 * 7/2007 Larsen et al. ................. 514/16.4
7,504,092 B2 * 3/2009 Dal Farra et al. ............ 424/70.1

FOREIGN PATENT DOCUMENTS
WO W093/25580 A 12/1993

OTHER PUBLICATIONS

Grieco et al. "Extensive structure—activity studies of lactam derivatives of MT-II and SHU-9119: their activity and selectivity at human melanocortin receptors 3, 4, and 5." J. Peptide Res., 2003, 62, 199-206.*
Peter W. Schiller et al., "Synthesis of side-chain to side-chain cyclized peptide analogs on solid supports", International Journal of Peptide and Protein Research, 1985, vol. 25, pp. 171-177 (8 pages).
Maria A. Bednarek et al., "Structure-function studies on the cyclic peptide MT-II, lactam derivative of alpha-melanotropin", Peptides, 1999, vol. 20, pp. 401-409; Elsevier (10 pages).
Ezz-Eldin M. Salem, "Solid-phase synthesis of a cyclic decapeptide, analog of the antibiotic Polymuxin M", Die Pharmazie, 1980, vol. 35 (12), pp. 761-763 (4 pages).
Maria Teresa Machini Miranda et al., "Transesterification of peptide esters and peptidyl resins in methanol-containing calcium acetate", International Journal of Peptide and Protein Research, 1991, vol. 37 (5), pp. 451-456 (6 pages).
Sylvie E Blondelle (ED), "Understanding biology using peptides"—Proceedings of the Nineteenth American Peptide Symposium, San Diego, California, Jun. 23, 2005, Springer, New-York (4 pages).
Fahed Al-Obeidi et al., "Potent and prolonged acting cyclic lactam analogues of alpha-melanotropin : design based on molecular dynamics", Journal of Medicinal Chemistry, 1989, vol. 32(12), pp. 2555-2561, American Chemical Society (8 pages).
David Flora et al., "Detection and Control of aspartimide formation in the synthesis of cyclic peptides." Bioorganic and Medicinal Chemistry Letters, 2005, vol. 15, pp. 1065-1068, Elsevier (4 pages).
N.E. Mealy, "PT-141" in Annual Update 2003/2004—Treatment of Genitourinary Disorders, Drugs of the Future (Journal), 2004, vol. 29(6), p. 645, Thomson Reuters (2 pages).
Miklos Bodanszky, Chapter II: "Activation and Coupling", in: Principles in Peptide Synthesis, 2nd Edition, Springer Verlag Berlin/Heidelberg, 1993, pp. 9-61 (29 pages).
J.Y. Savoie et al., "Solid-phase synthesis of selectively protected peptides : Use of thallous alkoxide as catalyst in the transesterification step", Canadian Journal of Chemistry, 1974, vol. 52, pp. 2832-2839 (8 pages).
PCT International Search Report dated Oct. 10, 2007 from ISA/EPO for International Application No. PCT/EP2007/057362 (4 pp.).
[Unknown Author], "Resins for Boc SPPS of peptide acids", NOVABIOCHEM 2002/3 Catalog, vol. 2002/3, 2002, p. 200, XP007916773, 1 pg.
R. Frenette, "Biaryl Synthesis via Suzuki Coupling on a Solid Support", Tetrahedron Letters, 1994, vol. 35, No. 49, pp. 9177-9180, 4 pgs.

* cited by examiner

*Primary Examiner* — Anish Gupta
(74) *Attorney, Agent, or Firm* — Mayer Brown LLP

(57) ABSTRACT

A process for manufacturing a cyclic peptide which comprises providing a cyclic peptide bonded to a Merrifield-type resin and cleaving the cyclic peptide from the Merrifield type resin by transesterification.

22 Claims, No Drawings

PROCESS FOR THE MANUFACTURE OF PEPTIDES

CROSS-REFERENCE TO RELATED APPLICATIONS

The present application is a U.S. national stage application under 35 U.S.C. 371 of International Application No. PCT/EP2007/057362 filed Jul. 17, 2007, which claims priority benefit of U.S. U.S. provisional patent application No. 60/832,649 filed on Jul. 21, 2006, the contents of these applications being herein incorporated by reference into the present application for all purposes.

The present application claims benefit of U.S. provisional 60/832,649, the contents of which is incorporated by reference into the present application.

The present invention concerns a process for the manufacture of peptides and intermediates useful therein.

Peptides are potentially biologically active and quite a lot of useful peptide-based drugs are known today. A particular example of a biologically active peptide is

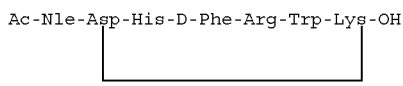

(PT-141) which is a candidate drug useful for treatment of erectile dysfunction (Drugs Fut 2004, 29(6), p. 645). Different synthetic approaches have been developed for this molecule. For example, Flora et al. Bioorg. Med Chem. Lett. 2005 (1065-1068) describes a solid phase peptide synthesis strategy for the molecule. However, this process requires use of costly Wang type resins and extremely costly protection and deprotection technology.

It is an object of the present invention to provide an industrializable process for manufacture of cyclic peptides having improved yield of cyclic product.

The invention concerns in consequence a process for manufacturing a cyclic peptide which comprises
(a) providing a cyclic peptide bonded to a Merrifield-type resin and
(b) cleaving the cyclic peptide from the Merrifield type resin by transesterification.

It has been found, surprisingly, that the process according to the invention allows for industrial scale manufacture of cyclic peptides or peptide derivatives with reagents having low cost. The cyclic peptide obtained in the process according to the invention has high purity and can be purified more easily, use of HF commonly used for removing peptide from Merrifield-type resins is avoided according to the process according to the invention. This is particularly advantageous, as the use of HF is an obstacle to industrial scale peptide synthesis with Merrifield-type resins.

For the purposes of the present invention "Merrifield-type resin" intends to denote in particular a chloromethylated styrene-divinylbenzene copolymer, which can optionally be substituted by substituents. An unsubstituted chloromethylated styrene-divinylbenzene copolymer is more particularly preferred.

In the process according to the invention, the cyclic structure of the cyclic peptide is generally formed by 2, 3, 4, 5, 6, 7, 8, 9, 10, 11, 12, 13 14, 15, 16, 17, 18, 19 or 20 amino acids. The cyclic structure of the cyclic peptide is preferably formed by 5, 6, 7, 8, 9, 10, 11 or 12 amino acids and more preferably by 6 or 7 amino acids.

In the process according to the invention, the cyclic peptide has preferably an amide bond formed through intramolecular reaction of a carboxylic group with an amino group.

In the process according to the invention, the transesterification is advantageously carried out with an alcohol or a mercaptane on particular an alkyl alcohol or an alkyl mercaptane, in particular a C1-C3 alcohol, preferably selected from methanol and ethanol. Methanol is more particularly preferred. Methanethiol or ethanethiol is preferred as mercaptane, in particular in the form of their alkali metal salts.

When the transesterification is carried out with an alcohol, the cyclized supported peptide is preferably suspended in the alcohol or in a mixture of the alcohol with a supplementary suitable solvent.

When the transesterification is carried out with a mercaptane, the cyclized supported peptide is preferably suspended in a solution of a salt of the mercaptane in a suitable solvent.

In the process according to the invention, a transesterification catalyst may suitably be used which can be selected, for example, from bases, in particular nucleophilic bases such as for example amines, in particular tertiary amines or sterically hindered alkoxides such as tert. alkoxides e.g potassium tert.-butoxide, anion-exchange resins in particular quaternary anion-exchange resins and alkalimetal salts of nuclephilic anions selected in particular from cyanides and fluorides such as potassium cyanide or potassium fluoride. Tertiary amines are preferred in particular diisopropylethyl amine and most preferably triethyl amine.

When a transesterification catalyst is used, its concentration in the mixture catalyst/solvent is generally from 0.5 to 3 mole/liter, preferably from 1 to 2.5 mole/liter and most preferably about 2 mole/liter.

In a particular embodiment, the transesterification is carried out with an aminoalcohol, in particular an aminoalcohol having a tertiary amine function and a primary alcohol function such as in particular 2-dimethylaminoethanol. In this embodiment use of supplemental catalyst is not required as the amino function catalyses the reaction. In this embodiment, the use of toxic catalysts such as thallium derivatives as in Savoie et al. Can J. Chem. 1974 p. 2832-9 can be avoided.

In the process according to the invention, the transesterification is generally carried out at a temperature of from 0° C. to 100° C. and preferably from 10° C. to 60° C. A temperature of about 25° C. is particularly preferred.

In the process according to the invention, the transesterification is generally carried out at atmospheric pressure.

In the process according to the invention, the free cyclic peptide acid can suitably be obtained from a cyclic peptide ester obtained in step (b) by reaction with a base selected for example from alkaline, quaternary ammonium or earth-alkaline metal hydroxides or carbonates. Particular examples include tetrabutylammonium hydroxide, potassium carbonate and lithium hydroxide. Lithium hydroxide is preferred.

In the process according to the invention, cleavage is generally carried out at a pH of from 8 to 10.

In the process according to the invention, the optional cleavage is generally carried out at a temperature of from 0° C. to 100° C. and preferably from 10° C. to 60° C. A temperature of about 25° C. is particularly preferred.

In a preferred embodiment, the invention concerns a process for manufacturing a cyclic peptide having an amide bond formed through intramolecular reaction of a carboxylic group with an amino group which comprises
(a) providing a linear peptide bonded to a Merrifield-type resin comprising a first amino acid having a free amino group and a second amino acid having a free carboxylic group (b) cyclizing the supported peptide by intramolecular reaction of the carboxylic group with the amino group
(c) cleaving the cyclized supported peptide from the Merrifield type resin by transesterification.

In this embodiment, the linear peptide is generally cyclized in the presence of an amide bond forming reagent. The amide bond forming reagent is suitably selected from coupling reagents for peptide synthesis known in the art such as those described in Bodansky, M., Principles of Peptide Synthesis, 2nd ed. Springer Verlag Berlin/Heidelberg, 1993. Particular examples of amide bond forming agents are selected from mixed anhydrides and other acylating agents such as activated esters or acid halogenides for example isobutyl-chloroformate or pivaloyl chloride. They may be carbodiimides (e.g. 1-ethyl-3-(3-dimethylaminopropyl)-carbodiimide), activated benzotriazine-derivatives (DEPBT: 3-(diethoxyphosphoryloxy)-1,2,3-benzotriazine-4(3H)-one) or uronium or phosphonium salt derivatives of benzotriazol.

A preferred amide bond forming reagent is dicylohexyl-carbodiimide. It has been found that this cheap reagent gives good results in the cyclization.

In an advantageous embodiment, the process according to the invention further comprises providing a precursor linear peptide having a protected amino group and a protected carboxylic group.

In this embodiment the amino group is protected by a first protective group. The first protective group is selected for example from protective groups which can be removed under conditions leaving the bond of the linear peptide to the Merrifield resin substantially intact. Preferred examples of such protective groups include amino protective groups which can be removed by acidolysis selected for example from t.butoxycarbonyl, para-methoxybenzyloxycarbonyl, benzhydryloxycarbonyl, and, preferably, benzyloxycarbonyl. Other examples of such protective groups include amino protective groups which can be removed by reduction with metals or metal compounds such as for example trichloroethoxycarbonyl.

In this embodiment, the carboxylic group is protected by a second protective group. The second protective group is selected for example from protective groups which can be removed under conditions leaving the bond of the linear peptide to the Merrifield resin substantially intact. Preferred examples of such protective groups include carboxyl protective groups which can be removed by acidolysis selected for example from para-methoxybenzyl, benzhydryl, and, preferably, t.butyl. Other examples of such protective groups include protective groups which can be removed by reduction with metals or metal compounds such as for example trichloroethyl.

In this embodiment, first and second protective groups are preferably selected to be removable in a single reaction step. Accordingly, the protective groups of the precursor peptide can be removed in a single reaction to provide the linear peptide. Examples of suitable combinations of first and second protective groups which can be removed by acidolysis a single reaction step include benzhydryloxycarbonyl/benzhydryl; para-methoxybenzyloxycarbonyl/para-methoxybenzyl and, preferably, t.butoxycarbonyl/t.butyl. Examples of suitable combinations of first and second protective groups which can be removed by reduction with metal or metal compounds in a single reaction step include trichloroethoxycarbonyl/trichloroethyl When the removal of protective groups is carried out by acidolysis, suitable reagents are selected for example from perfluoroalkyl carboxylic acids and solutions of HCl in organic solvents preferably polar organic solvents such as dioxane or ethyl acetate. Trifluoroacetic acid is preferred as reagent for acidolysis.

When the removal of protective groups is carried out by reaction with a metal or metal compound, a suitable reagent is, for example, zinc metal.

The process according to the invention is particularly suitable when the linear peptide comprises an amino acid having a side chain containing an amino group. Examples of amino acid having a side chain containing an amino group include lysine, ornithine, diaminobutyric acid and diaminopropionic acid. A preferred example of amino acid having a side chain containing an amino group is lysine.

In a particularly preferred embodiment, the linear peptide is bonded to the Merrifield resin through the amino acid having a side chain containing an amino group.

In the process according to the invention the linear peptide can suitably comprise an amino acid having a side chain containing a carboxylic group. Examples of amino acids having a side chain containing a carboxylic group include glutamic acid and aspartic acid. A preferred example is aspartic acid.

In a particularly preferred aspect, the linear peptide comprises both an amino acid having a side chain containing a carboxylic group and an amino acid having a side chain containing an amino group.

The sequence

Ac-Nle-Asp-His-D-Phe-Arg-Trp-Lys-Merrifield resin is more particularly preferred The side chain carboxylic group or side chain amino group can be suitably protected by the respective protective groups described above.

The invention concerns in particular a process for the manufacture of

Ac-Nle-Asp-His-D-Phe-Arg-Trp-Lys-OH
        |_____| which comprises providing

Ac-Nle-Asp-His-D-Phe-Arg-Trp-Lys-Merrifield resin, cyclizing the supported peptide by intramolecular reaction of the carboxylic group with the amino group and cleaving the cyclized supported peptide from the Merrifield type resin by transesterification. The transesterification is generally followed by an operation to cleave the ester such as in particular a saponification to yield the cyclic peptide acid.

The invention also concerns a cyclic peptide which is bonded to a Merrifield-type resin. The supported cyclic peptide according to the invention is preferably as described herein before.

The invention also concerns

P-Nle-Asp-His-D-Phe-Arg-Trp-Lys-Merrified resin
       |_____| wherein P is an amino protecting group, in particular an acyl group and preferably an acetyl group (Ac).

The invention also concerns

```
P-Nle-Asp-His-D-Phe-Arg-Trp-Lys-Merrifield resin
``` wherein P is as defined here before.

The example here after is intended to illustrate the invention in a non-limitative manner:

The abbreviations used herein are as follows:
Ac Acetyl
Nle Norleucine
Asp Aspartic acid
His Histidine
Phe Phenylalanine
Arg Arginine
Trp Tryptophan
Lys Lysine
HF Hydrogen Fluoride
Fmoc 9-Fluorenylmethyloxycarbonyl
Boc t-butyloxycarbonyl
RCM resin chloromethyl (Merrifield resin)
SPPS Solid phase peptide synthesis
Pbf 2,2,4,6,7-Pentamethyldihydrobenzofuran-5-sulfonyl
Trt trityl
tBu t-butyl
TFA trifluoroacetic acid
DI distilled
TIPS triisopropylsilane
DTE dithioerythreitol
DCM dichloromethane
IPA isopropanol
DIEA diisopropylethylamine
DMF dimethylformamide
HOBT hydroxybenzotriazole
DCC dicyclohexylcarbodiimide
TEAP triethylammonium phosphate
LiOH Lithium hydroxide

EXAMPLE

```
Sequence: Ac-Nle-Asp-His-D-Phe-Arg-Trp-Lys-OH
```

Synthesis:
50 g Fmoc-Lys(Boc)-RCM resin (Subst. 0.8 mmol/g) used for synthesis. Fmoc SPPS strategy used for synthesis at a concentration of 10 ml/gm.

The following Amino acid derivatives used for synthesis:
Fmoc-Trp(Boc)-OH
Fmoc-Arg(Pbf)-OH
Fmoc-D-Phe-OH
Fmoc-His(Trt)-OH
Fmoc-Asp(OtBu)-OH
Fmoc-Nle-OH
Deprotection
Acetylation utilizing Acetic anhydride Deprotection of peptide on the resin by utilizing the following reagent: 84% TFA, 5% Anisole, 5% DI water, 3% Thioanisole, 3% TIPS containing 2% DTE. Cleaved for 1 to 2 hours.

Washing Procedure Used After Cleavage:
2×DCM
1×IPA
2×5% DIEA in DCM for 4 minutes each (check pH paper)
1×DCM
2×Methanol
2×DCM
1×DMF Cyclization on the resin by using 5 eq. HOBT/10 eq. DCC in DMF for 48 hours-72 hours.

The Peptide was cleaved from the resin utilizing the following procedure: Peptide resin stirred for 2 days at ambient temperature in 15% TEA in Methanol. After cleavage from the resin 5% DI water and 5 eq. LiOH added and continued to stir for 2 hours. Acetic acid was added to acidify reaction mixture. Resin filtered off and washed with TFA A Buffer containing 30% Acetonitrile. Filtrate evaporated or diluted with TFA A Buffer until organic solvent component was below 20%. Solution filtered and purified.

Purification:
TEAP system and then Acetic acid system to yield 5.0486 g pure CS341 (HPLC>99%)

Overall yield: 12.3%

The invention claimed is:

1. A process for manufacturing a cyclic peptide comprising the steps of:
    (a) providing a cyclic peptide bonded to a Merrifield-type resin and
    (b) cleaving the cyclic peptide from the Merrifield type resin with a transesterification reagent.

2. The process according to claim 1, wherein the transesterification reagent comprises a C1-C3 alcohol.

3. The process according to claim 1, wherein the transesterification reagent comprises an alkyl thio or a salt thereof.

4. The process according to claim 1, wherein the cleaving step is carried out at a pH of between approximately 8 and 10.

5. The process according to claim 1, wherein the cyclic structure of the cyclic peptide is formed by 3, 4, 5, 6, 7, 8, 9, 10, 11, 12, 13 14, 15, 16, 17, 18, 19 or 20 amino acids.

6. The process according to claim 1, wherein the cyclic peptide is bonded to the Merrifield-type resin through an amino acid which forms part of the cyclic structure.

7. The process according to claim 1, wherein the cyclic peptide comprises an amide bond formed through intramolecular reaction of a carboxylic group with an amino group.

8. The process according to claim 1, wherein the cyclic peptide bonded to the Merrifield resin is provided by:
    (a) providing a linear peptide bonded to the Merrifield-type resin, wherein the linear peptide comprises a first amino acid having a free amino group and a second amino acid having a free carboxylic group; and
    (b) cyclizing the linear peptide bonded to the Merrifield-type resin by intramolecular reaction of the free carboxylic group with the free amino group.

9. The process according to claim 8, wherein the linear peptide is cyclized in the presence of an amide bond forming reagent selected from the group consisting of mixed anhydrides, activated esters, acid halogenides, carbodiimides, activated benzotriazine-derivatives, uranium salt derivatives of benzotriazol, and phosphonium salt derivatives of benzotriazol.

10. The process according to claim 8, further comprising providing a precursor linear peptide bonded to the Merrifield-type resin, wherein the precursor linear peptide comprises a protected amino group and a protected carboxylic group.

11. The process according to claim 10, wherein the protected amino group of said precursor linear peptide is protected by a first protective group selected from the group consisting of butoxycarbonyl, para-methoxybenzyloxycarbonyl, benzhydryloxycarbonyl, or benzyloxycarbonyl, and wherein the carboxylic group is protected by a second protective group selected from the group consisting of para-methoxybenzyl, benzhydryl, and t-butyl.

12. The process according to claim 11, wherein the process further comprises the step of removing the first amino protective group and the second carboxyl protective group by reaction with trifluoroacetic acid.

13. The process according to claim 10, wherein the protected amino group of said precursor linear peptide is protected by a first protective group removable by reduction with a metal or metal compound; and wherein the protected carboxylic group is protected by a second protective group removable by reduction with a metal or metal compound.

14. The process according to claim 13, wherein the process further comprises the step of deprotecting the protected amino group and the protected carboxyl group by reaction of the first and second protective groups with zinc metal.

15. The process according to claim 10, wherein the amino group and the carboxylic group of the precursor linear peptide are protected respectively by a first protective group and a second protective group which are removable, and wherein the first and second protective groups of the precursor linear peptide are removed in a single reaction to provide said linear peptide.

16. The process according to claim 8, wherein the linear peptide bonded to the Merrifield-type resin comprises an amino acid having a side chain containing an amino group.

17. The process according to claim 16, wherein the amino acid having a side chain containing an amino group is lysine.

18. The process according to claim 16, wherein the linear peptide is bonded to the Merrifield resin through the amino acid having a side chain containing an amino group.

19. The process according to claim 8, wherein the linear peptide comprises an amino acid having a side chain containing a carboxylic group.

20. The process according to claim 1, wherein the cleaving step is followed by hydrolysis to yield a cyclic peptide acid.

21. The process according to claim 1, wherein the cyclic peptide bonded to the Merrifield-type resin is

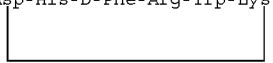

Merrified-type resin.

22. The process according to claim 1, wherein the cyclic peptide bonded to the Merrifield-type resin is

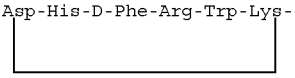

Merrified-type resin, wherein P is an amino protecting group.

* * * * *